(12) United States Patent
Santelli, Jr.

(10) Patent No.: US 7,090,652 B2
(45) Date of Patent: Aug. 15, 2006

(54) REUSABLE CERVICAL COLLAR HAVING A CHIN STRAP MEMBER FASTENING ELEMENT WITH A PULL CORD

(76) Inventor: Albert Santelli, Jr., 58 Hillcrest Rd., Martinsville, NJ (US) 08836

( * ) Notice: Subject to any disclaimer, the term of this patent is extended or adjusted under 35 U.S.C. 154(b) by 355 days.

(21) Appl. No.: 10/224,990

(22) Filed: Aug. 22, 2002

(65) Prior Publication Data
US 2004/0039318 A1    Feb. 26, 2004

(51) Int. Cl.
*A61F 5/00*    (2006.01)
(52) U.S. Cl. .................. 602/18; 128/DIG. 23
(58) Field of Classification Search .......... 602/18, 602/5, 6, 17–19, 23, 27; 128/DIG. 23
See application file for complete search history.

(56) References Cited

U.S. PATENT DOCUMENTS

| | | | | |
|---|---|---|---|---|
| 2,818,063 A * | 12/1957 | Smith et al. | ........... | 602/18 |
| 3,530,853 A * | 9/1970 | Bond | ........... | 602/18 |
| 3,916,885 A * | 11/1975 | Gaylord, Jr. | ........... | 602/18 |
| 4,413,619 A * | 11/1983 | Garth | ........... | 602/18 |
| 4,677,969 A * | 7/1987 | Calabrese | ........... | 602/18 |
| 5,038,759 A * | 8/1991 | Morgenstern | ........... | 602/18 |
| 5,215,517 A * | 6/1993 | Stevenson et al. | ........... | 602/18 |
| 5,230,698 A * | 7/1993 | Garth | ........... | 602/18 |
| 5,520,619 A * | 5/1996 | Martin | ........... | 602/5 |
| 5,588,957 A * | 12/1996 | Martin, Sr. | ........... | 602/18 |
| 5,622,529 A * | 4/1997 | Calabrese | ........... | 602/18 |
| 5,632,722 A * | 5/1997 | Tweardy et al. | ........... | 602/18 |
| 5,688,229 A * | 11/1997 | Bauer | ........... | 602/18 |
| 5,728,054 A | 3/1998 | Martin | ........... | 602/18 |
| D393,718 S | 4/1998 | Traut et al. | ........... | D24/191 |
| 5,785,670 A | 7/1998 | Hiebert | ........... | 602/18 |
| 5,795,315 A * | 8/1998 | Traut et al. | ........... | 602/18 |
| 5,797,863 A * | 8/1998 | Kohnke | ........... | 602/18 |
| 5,904,662 A | 5/1999 | Myoga | ........... | 602/18 |
| 5,950,627 A * | 9/1999 | Bologovsky et al. | ........... | 128/869 |
| 5,993,403 A | 11/1999 | Martin | ........... | 602/18 |
| 6,036,664 A | 3/2000 | Martin, Sr. et al. | ........... | 602/5 |
| 6,045,523 A * | 4/2000 | Donaldson | ........... | 602/18 |
| 6,050,965 A | 4/2000 | Pillai | ........... | 602/18 |
| 6,056,711 A | 5/2000 | Domanski et al. | ........... | 602/18 |
| RE36,745 E * | 6/2000 | Rudy et al. | ........... | 602/18 |
| 6,071,255 A | 6/2000 | Calabrese | ........... | 602/18 |
| 6,090,058 A | 7/2000 | Traut et al. | ........... | 602/18 |
| 6,245,033 B1 | 6/2001 | Martin | ........... | 602/18 |
| 6,254,560 B1 * | 7/2001 | Tweardy et al. | ........... | 602/18 |
| 6,423,020 B1 * | 7/2002 | Koledin | ........... | 602/18 |
| 6,494,854 B1 * | 12/2002 | Visness et al. | ........... | 602/18 |
| 6,669,427 B1 * | 12/2003 | Santelli, Jr. | ........... | 411/510 |

* cited by examiner

*Primary Examiner*—Danton D. DeMille
*Assistant Examiner*—Huong Q. Pham
(74) *Attorney, Agent, or Firm*—Duane Morris LLP

(57) ABSTRACT

A cervical collar including a collar member, a chin strap member having a first arm attached to the collar member; and a fastening element coupled to a second arm of the chin strap member. The fastening element attaches the second arm of the chin strap member to the collar member at a time of use. The fastening element includes a pull cord member that pulls the fastening element into an aperture in the collar member to attach the second arm of the chin strap member to the collar member at the time of use. One or more of the components of the collar may be made from materials having an antimicrobial additive which enable the cervical collar to be reused.

16 Claims, 5 Drawing Sheets

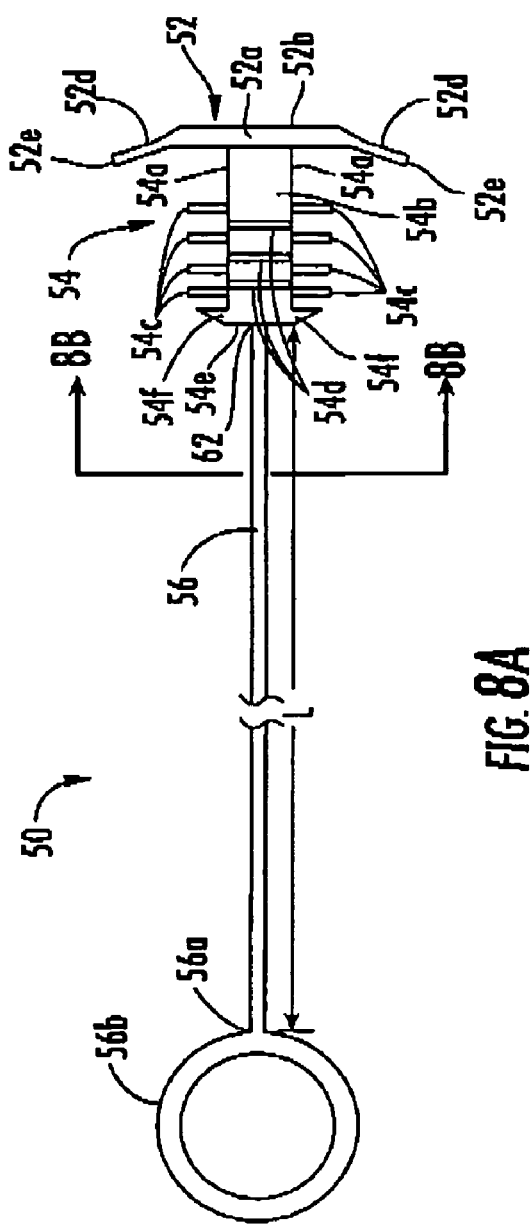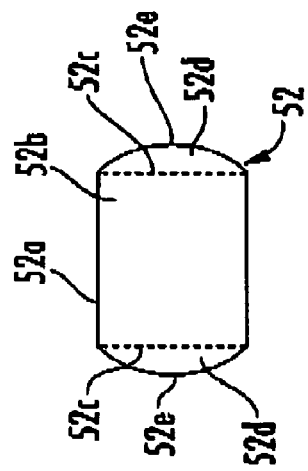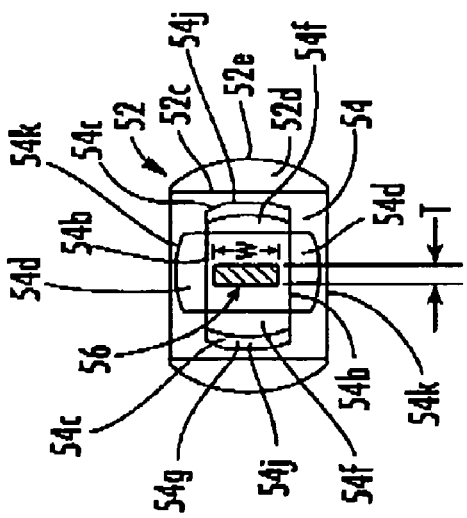
FIG. 8A
FIG. 8C
FIG. 8B

REUSABLE CERVICAL COLLAR HAVING A CHIN STRAP MEMBER FASTENING ELEMENT WITH A PULL CORD

RELATED APPLICATIONS

U.S. patent application Ser. No. 10/224,939, entitled "FASTENING ELEMENT HAVING A FLEXIBLE PULL CORD", filed Aug. 21, 2002, now U.S. Pat. No. 6,669,427.

FIELD OF THE INVENTION

This invention relates to cervical collars. More specifically, this invention relates to a reusable cervical collar including a fastening element with a pull cord member that facilitates complete assembly of collar at the time of use.

BACKGROUND OF THE INVENTION

There are many types of cervical collars that are designed to restrict movement of the head and neck of a person who has suffered a neck or spinal injury. More recent cervical collars are generally constructed from relatively stiff, lightweight plastic materials that are capable of being bent to encircle the neck of the injured patient and yet still provide substantial support for the patient.

Cervical collars commonly include an elongated neck encircling collar member and a strap-like chin support member attached to the collar member. The chin support member of the collar is located under the patient's chin after the collar member of the collar has been positioned around the neck of the patient. The chin support member is typically formed with a snap-fastening element that is snapped into a corresponding aperture in the collar member to secure the free end of the chin support member to the collar member. The other end of the chin support member is attached to the collar member during the manufacturing process.

It is sometimes difficult in an emergency medical situation to insert the fastening element into the aperture in the collar member to secure the free end of the chin support member thereto, after the collar member is positioned around the neck of the patient. Fastening the chin support member to the collar member before the collar member is positioned around the patient's neck makes the application of the collar member difficult and uncomfortable for the patient, as the patient's head body may need to be moved slightly to fit the collar member around the patient's neck.

Further, present cervical collars are typically discarded after a single use, especially if they become contaminated with blood or other bodily fluids, thus increasing the costs of emergency medical services. This is because conventional cervical collars must be sterilized in a relatively expensive process, after the blood or other bodily fluid is wiped from the surfaces of the collar.

Accordingly, there is a need for a reusable cervical collar that has a chin support fastening element which is easily accessed and operated.

SUMMARY OF THE INVENTION

Summarily described is a cervical collar comprising a collar member, a chin strap member having a first arm attached to the collar member; and a fastening element coupled to a second arm of the chin strap member. The fastening element attaches the second arm of the chin strap member to the collar member at a time of use. The fastening element includes a pull cord member that pulls the fastening element into an aperture in the collar member to attach the second arm of the chin strap member to the collar member at the time of use. The fastening element permits the collar member to be positioned around the neck of a patient from a flat storage position and the chin strap member to be easily positioned and secured minimal movement of the patient.

In one embodiment of the invention, the collar and chin strap members may be made from plastic sheet material having an antimicrobial additive, which enables the cervical collar to be reused.

BRIEF DESCRIPTION OF THE DRAWINGS

FIGS. 4–7 depict the use of the fastening element of the present invention to facilitate complete assembly of the chin strap member to the collar member at the time of use wherein FIGS. 4 and 6 are front elevational views of the cervical collar and FIGS. 5 and 7 are rear elevational views of the cervical collar.

FIG. 8A is an elevational view of the fastening element of the present invention.

FIG. 8B is an end view of the fastening element of FIG. 8A looking toward the head of the fastening element.

FIG. 8C is a sectional end view through line 8C—8C of the fastening element of FIG. 8A.

DETAILED DESCRIPTION OF THE INVENTION

Figure 1:
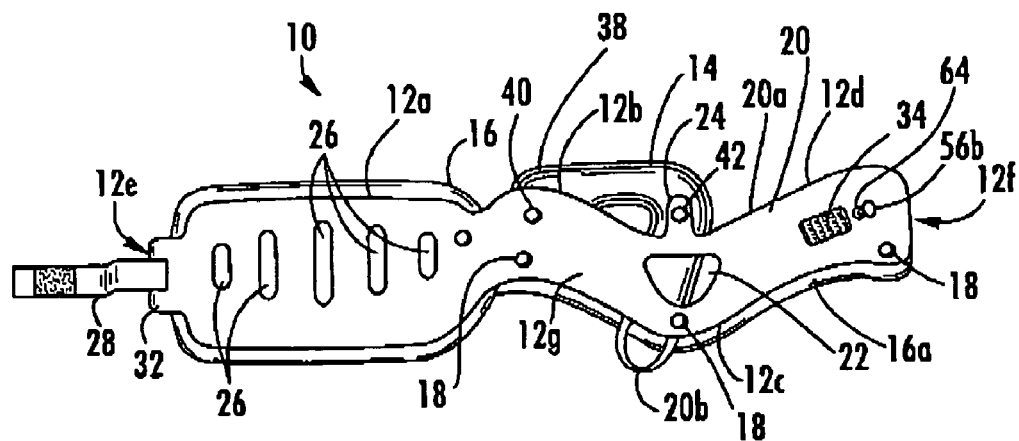
FIG. 1 is a front elevational view of a cervical collar made according to an exemplary embodiment of the present invention.
Figure 2:
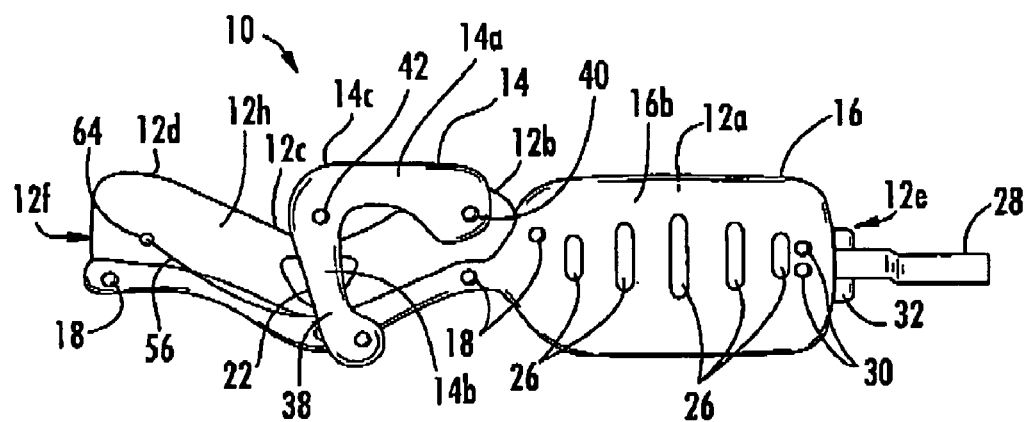
FIG. 2 is a rear elevational view of the cervical collar of FIG. 1.

Referring collectively to FIGS. 1 and 2, there is shown a cervical collar 10 made according to an exemplary embodiment of the present invention. The collar 10 generally comprises an elongated collar member 12, that is capable of being rolled to encircle the neck of a patient, and a chin strap member 14, which supports the chin of the patient.

The collar member 12 is typically constructed as a unitary, asymmetrical component comprised of a back portion 12a, a first side portion 12b, a front portion 12c, and a second side portion 12d. The free end of the back portion defines a first end 12e of the collar member 12 and the free end of the second side portion 12d defines a second end 12f of the collar member 12. In use, the front portion 12c, which has affixed to it a center portion 14c of the chin strap member 14, is located in the front of the patient's neck under the patient's chin, and the back portion 12a of the collar member 12 is placed behind the back of the patient's neck.

The collar member 12 is typically formed from somewhat rigid, plastic sheet material, such as high density polyethylene. The collar member may be die cut or injection molded as is conventional in the industry. Although the plastic sheet material is somewhat rigid, it is still flexible enough to be rolled so that when it is formed into the collar member 12, the collar member 12 can be placed around the patient's neck.

Still referring to FIGS. 1 and 2, the collar member 12 has an outer surface 12g and an inner surface 12h. The portions of the inner surface 12h of the collar member 12 which come into contact with the patient's body or head are covered by at least one pad element 16. The pad element 16 is formed conventionally from foam using die cutting or the like. The pad element 16 prevents the inner surface 12h and the edges of the collar member 12 from pressing and rubbing uncomfortably against the patient's body and head. The pad element 16 is secured to the inner surface 12h of the collar member 12 with snap fasteners 18 that extend through apertures (not visible) in the collar member 12 and the pad element 16. One of ordinary skill in the art will of course recognize that any other conventional securing means can be used to secure the pad element 16 to the inner surface 12h of the collar member 12.

The front portion 12c and the first and second side portions 12b and 12d of the collar member 12 form a V-shape section 20 with a concave upper edge 20a and a convex lower edge 20b. A strip-like portion 16a of the pad element 16 extends along the lower portion of the V-shape section 20 on the inner surface 12h of the collar 12. The strip-like portion 16a of the pad 16 overlaps the convex lower edge 20b of the V-shape section 20 but generally follows the contour of the lower edge 20b. The front portion 12c of the collar member 12 includes an opening 22, which in use, exposes the patient's larynx to permit a tracheotomy to be performed therethrough with the cervical collar 10 in place. The concave upper edge 20a of the V-shaped section 20 (formed by the front portion 12c) includes an upwardly extending chin strap support tab 24. The chin strap support tab (30) is used for securing the chin strap member 14 to the front portion 12c of the collar member 12 as will be described further on in greater detail.

The back portion 12a of the collar member 12 typically has a generally rectangular or oval shape. The portion 16b of the pad element that is secured to the inner surface 12h of the back portion 12a of the collar member 12, overlaps the edges of the back portion 12a. A plurality of air holes 26 extend through the back portion 12a and its corresponding portion 16b of the pad element 16. The air holes 26 may be elongated as shown, or formed in other conventional configurations.

A collar retaining strap 28 is attached adjacent the free end of the back portion 12a of the collar member 12 by push fasteners 30 that extend through apertures (not visible) in the strap 28, back portion 12a and the pad element 16. The strap 28 passes through a loop tab 32 extending from the free end of the back portion 12a. The retaining strap 28 cooperates with strap retaining means 34 associated with the second side portion 12d of the collar member 12 to couple the back portion 12a of the collar member 12 to the second side portion 12d of the collar member 12 to hold the cervical collar 10 securely in place around the neck of the patient. The collar retaining strap 28 can be implemented with any suitable choice of straps or fasteners. In the shown embodiment, the retaining strap 28 comprises a hook and loop fastener strip. The strap retaining means 34 comprise a corresponding hook and loop fastener strip secured to the outer surface 12g of the collar member 12 where the front portion 12c and second side portion 12d merge together.

The chin strap member 14 has first and second arms 14a, 14b that form an inverted V-shape. The chin strap member 14 is typically formed from rigid, plastic sheet material, such as high density polyethylene. The chin strap member 14 may be die cut or injection molded as is conventional in the industry. A second pad element 38 is secured to an inner surface (not visible) of the chin strap member 14, and overlaps the edges of this member 14. The chin strap member 14 is partially assembled to the collar member 12 to allow flat packaging and storage of the collar 10. Specifically, the end of the first arm 14a is attached to the first side portion 12b of the collar member 12 by a push fastener 40 that extends through apertures (not visible) in the first arm 14a, second pad element 38, and first side portion 12b. The center portion 14c of the chin strap member 14, where the first and second arms 14a, 14b meet is attached to the chin support tab 24 with a push fastener that extends through apertures (not visible) in the center portion 14c of the strap member 14, the second pad element 38 and the chin strap support tab 24.

Figure 3:
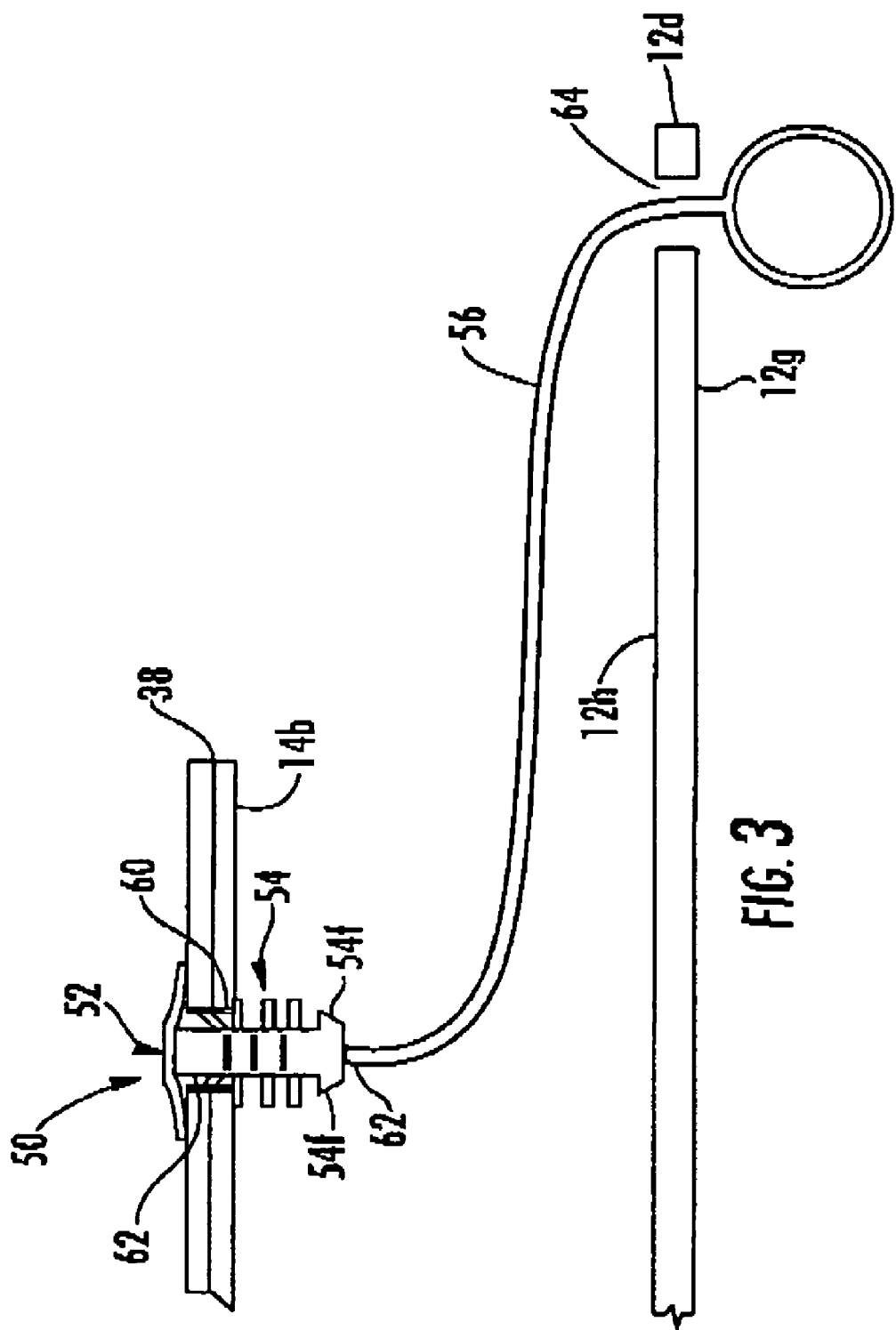
FIG. 3 is a sectional view through portions of the collar and chin strap members of the cervical collar of FIGS. 1 and 2.

As shown in FIGS. 1–3, the end of the second arm 14b of the chin strap member 14 is located near the bottom of the front portion 12 of the collar member 12 in the partially assembled state. The second arm 14b includes a quick assembly fastening element 50 that facilitates assembly of the second arm 14b to the collar member 12. The fastening element 50 extends through apertures (not visible) in the second pad element 38 and second arm 14b. The fastening element 50 includes a flexible pull cord 56 that extends through an aperture 54 in the second side portion 12d of the collar member 12.

As shown collectively in FIGS. 8A–8C, the fastening element 50 generally comprises a head 52, a shank 54 depending from the head 52 and a flexible pull cord 56 extending from the shank 54. The head 52 of the fastening element 50 includes a rigid central portion 52a having a substantially planar top surface 52b formed in a rectangular configuration, and opposing, tapered, flanges 52d extending downwardly from two opposing sides 52c of the central portion 52a. The leading edge 52e of each flange 52d is arcuately formed to define a convex edge shape. The flanges 52d are thinner than the central portion 52a and therefore, flexible relative thereto. Accordingly, the flanges 52d abut against the portion of the second pad element 38 that covers the second arm 14b of the chin strap member 14.

It should be understood that the head 52 shown and described herein is exemplary, and that the fastening element 50 may utilize any suitable well known head design.

The shank 54 of the fastening element 50 is a rigid, elongated member having a generally square cross-sectional configuration that defines a first pair of substantially planar, axially extending opposing side surfaces 54a and a second pair of substantially planar, axially extending opposing side surfaces 54b. The opposing side surfaces 54a each include a plurality of equally-spaced flexible gripping fingers 54c and the opposing side surfaces 54b each include a plurality of equally-spaced flexible gripping fingers 54d. The gripping fingers 54c and 54d extend outwardly from, and generally perpendicular to their respective side surfaces 54a and 54b, and have respective arcuate terminal edges 54j and 54k. The gripping fingers 54c and 54d are disposed in an alternating, staggered manner such that the gripping fingers 54c on the opposing side surfaces 54a are disposed in planes that lie between the planes of the gripping fingers 54d disposed on the opposing side surfaces 54b.

A pair of substantially rigid, lead-in elements 54f are formed laterally adjacent the free end surface 54e of the shank 54. The lead-in elements 54f extend from the opposing side surfaces 54a and have arcuate terminal edges 54g.

Figure 9A:
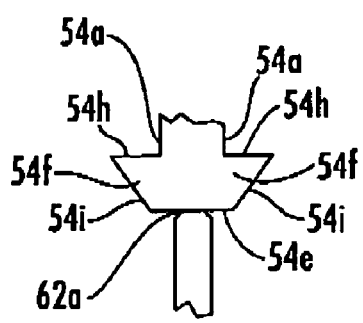
FIG. 9A is a partial view of the shank and pull cord showing a frangible connection according to first exemplary embodiment of the present invention at the pull cord shank interface, for removably coupling the pull cord to the shank.

As shown in FIG. 9A, each lead-in element 54f has a trailing surface 54h that extends perpendicular to the side surface 54b, and an inclined leading surface 54i that leans back toward the trailing surface 54h.

It should be understood that the shank 54 shown and described herein is exemplary, and that the fastening element 50 of the invention may utilize any suitable well known shank design.

Referring again to FIG. 3, the lead-in elements 54f facilitate entry into an aperture 62 in the second pad element 38, an aperture 60 in the second arm 14b of the chin strap member 14, and a corresponding aperture 64 formed in the second side portion 12d of the collar member 12. The gripping fingers 54c and 54d retain the fastening element 50 in the apertures 60, 64 of the chin strap member second arm 14b and the collar member second side portion 12d, to secure these structures together but can be forcibly withdrawn from one or both of the apertures 60, 64, when it is desired to separate these structures from one another.

Figure 9B:
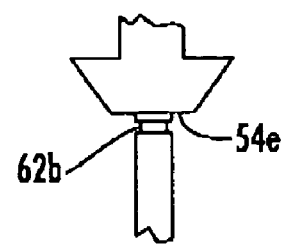
FIG. 9B is a partial view of the shank and pull cord showing a frangible connection according to a second exemplary embodiment of the present invention adjacent the pull cord shank interface, for removably coupling the pull cord to the shank.

The flexible pull cord 56 extends from the free end surface 54e of the shank 54. The flexible pull cord 56 may be rectangular in cross-section and formed in any desired length, width, and thickness. In one exemplary embodiment, the flexible pull cord may be about 8 inches in length (L in FIG. 8A), about 0.100 inches wide (W in FIG. 8B), and about 0.050 inches thick (T in FIG. 8C). The flexible pull cord 56 is preferably made detachable from the end surface 54e of the shank 54. Depending upon the material used for making the fastening element 50 and the cross-sectional area of the pull cord 56, no special frangible connection structure is typically required to facilitate detachment of the pull cord 56 from the end surface 54e of the shank 54. If necessary, however, a frangible connection 62 at or near the pull cord shank interface may be provided. The frangible connection 62 may be formed by an area 62a having a reduced cross-section (FIG. 9A), a score line 62b (FIG. 9B), or by any other conventional frangible connection. The terminal end 56a of the pull cord 56 is terminated with a flexible, finger grasping member 56b for manually grasping the pull cord with one's fingers. The grasping member 56b may be ring-shaped as in the shown embodiment, or any other suitable shape or design. The flexible grasping member 56b can be bent into a shape that allows it to be threaded through the apertures formed in the second arm 14b, second pad element 38, and the second side portion 12d of the collar member 12 so that it lies adjacent the outer surface 12g of the collar member 12.

The fastening element 50 is typically constructed as a unitary structure from a suitable plastic material, such as nylon, high density polyethylene, or polypropylene and can be made using conventional plastic forming methods, for example, injection molding.

Figure 4:
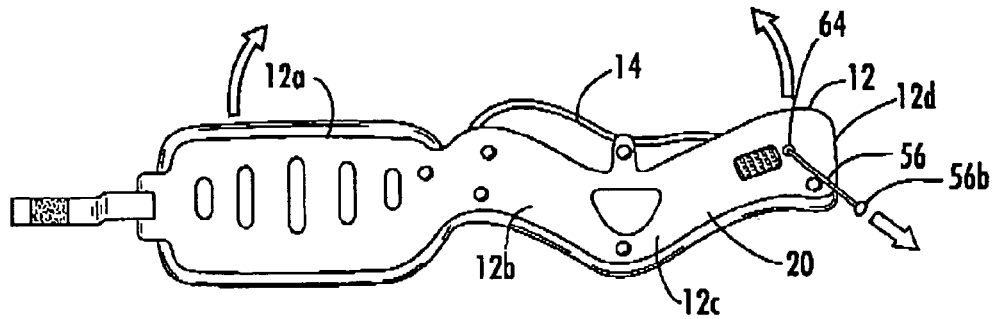
Figure 5:
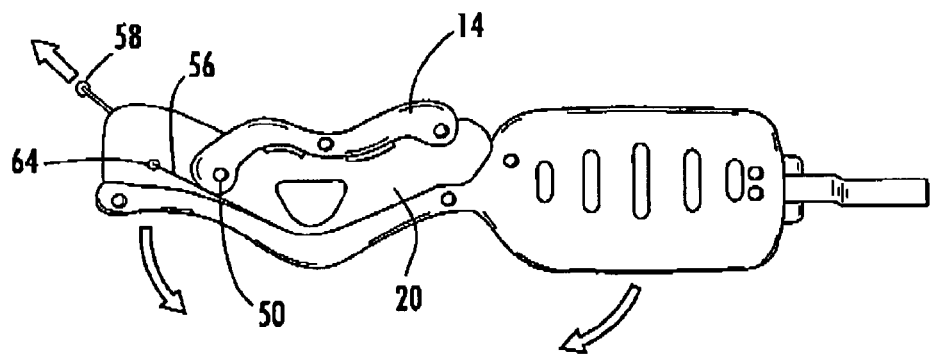
Figure 6:
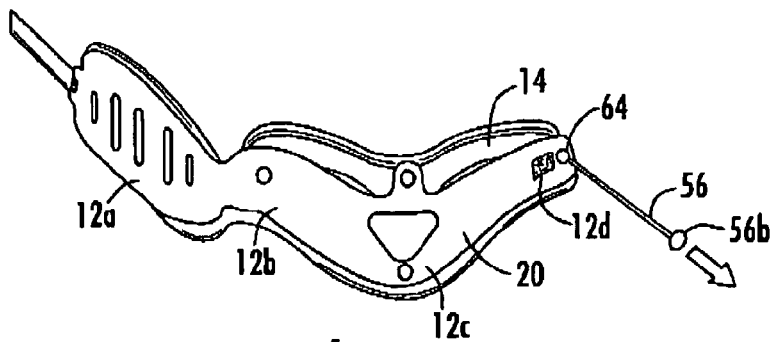
Figure 7:
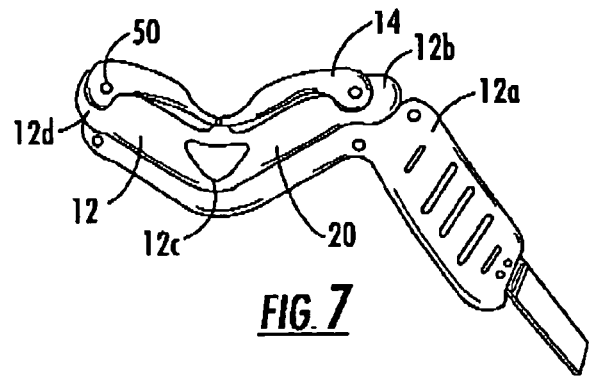

As shown in FIGS. 4–7, the fastening element 50 is used to facilitate complete assembly of the chin strap member 14 to the collar member 12 at the time of use. In FIGS. 4 and 5, the grasping member 56b of the pull cord 56 is grasped and pulled to bend the chin strap member 14 and the V-shape section 20 of the collar member 12 into a curvilinear, operational shape. In FIGS. 6 and 7, continued pulling the pull cord 56 moves the second arm 14b of the chin strap member 14 into position against the second side portion 12d of the collar member 12 and pulls the stud 54 of the fastening element 50 into the corresponding aperture 64 in the second side portion 12d of the collar member 12, thereby securing the second arm 14b of the chin strap member 14 to the collar member 12 and completing the assembly of the collar 10. The fully assembled collar 10 can then be placed around the patient's neck and secured with the collar retaining strap 28. The pull cord 56 can then be detached from the fastening element 50 by, for example, bending it back and forth at the end surface 54e of the shank 54 (or at the frangible connection 62), until it detaches therefrom.

The plastic sheet material used for forming the collar member 12 and the chin strap member 14, and the foam used for forming the pad elements, may include a non-leaching, antimicrobial additive that continuously wards off a wide variety of commonly occurring bacteria, fungi, and yeast the surfaces of the collar member. The antimicrobial additive combines silver with a zeolite ceramic. A preferred antimicrobial additive is Agion™ Silver Antimicrobial Type AJ10D, which is manufactured and sold by Agion™ Technologies. The antimicrobial may be introduced into the plastic sheet material by compounding it directly into the plastic pellets used for extruding or molding the plastic sheet material or mixing it with the plastic pellets during extrusion or the molding process. At least 0.3 percent by weight of the antimicrobial is compound into or mixed with the plastic pellets. The antimicrobial additive may be incorporated into the sheet material at up to 5.0 percent by weight.

The fastening element and/or the other fasteners may also be made from a material such as plastic, which includes the antimicrobial.

The antimicrobial additive in the sheet material allows the collar to be reused for other patients by merely wiping the surfaces of the collar with a suitable towel like cleaning device. Sterilization of the collar member is not required due to the antimicrobial properties of the plastic sheet material.

While the foregoing invention has been described with reference to the above embodiments, various modifications and changes can be made without departing from the spirit of the invention. Accordingly, all such modifications and changes are considered to be within the scope of the appended claims.

What is claimed is:

1. A cervical collar comprising:
   a collar member;
   a chin strap member having a first arm attached to the collar member; and
   a fastening element coupled to a second arm of the chin strap member, the fastening element for attaching the second arm of the chin strap member to the collar member at a time of use, the fastening element including a stud having a first end terminated with a head and a second end coupling a pull cord member that pulls the fastening element into an aperture in the collar member to attach the second arm of the chin strap member to the collar member at the time of use,
   wherein the pull cord is detachable from the fastening element.

2. The cervical collar according to claim 1, wherein the pull cord is associated with a frangible area to facilitate detachment of the pull cord from the fastening element.

3. A cervical collar comprising:
   a collar member;
   a chin strap member having first and second arms, the first arm attached to the collar member in a partially assembled state and a fully assembled state, the second arm detached from the collar member in the partially assembled state and attached to the collar member in the fully assembled state; and
   a fastening element coupled to the second arm of the chin strap member, the fastening element for attaching the second arm of the chin strap member to the collar member in the fully assembled state, the fastening element including a stud having a first end terminated with a bead and a second end coupling a pull cord member that pulls the fastening element into an aperture in the collar member to attach the second arm of the chin strap member to the collar member in the fully assembled state.

4. The cervical collar according to claim 1, wherein the pull cord extends through the aperture in the collar member.

5. The cervical collar according to claim 4, wherein the pull cord is terminated with a grasping member for manually grasping the end of the pull cord.

6. The cervical collar according to claim 3, wherein the pull cord is terminated with a grasping member for manually grasping the end of the pull cord.

7. The cervical collar according to claim 3, wherein the collar and chin strap members are made from plastic sheet material having an antimicrobial additive.

8. The cervical collar according to claim 3, further comprising a pad element attached to an inner surface of the collar member.

9. The cervical collar according to claim 8, further comprising a pad element attached to an inner surface of the chin strap member.

10. The cervical collar according to claim 3, further comprising a pad element attached to an inner surface of the chin strap member.

11. The cervical collar according to claim 3, wherein the stud further includes a plurality of spaced apart, flexible gripping elements.

12. The cervical collar according to claim 11, wherein the stud includes a rigid lead-in element adjacent the second end thereof.

13. The cervical collar according to claim 3, wherein the stud includes a rigid lead-in element adjacent the second end thereof.

14. The cervical collar according to claim 9, wherein the pad elements are made from a foam material having an antimicrobial additive.

15. The cervical collar according to claim 10, wherein the pad element is made from a foam material having an antimicrobial additive.

16. The cervical collar according to claim 3, wherein the fastening element is made from a plastic material having an antimicrobial additive.

* * * * *